(12) United States Patent
Reetz et al.

(10) Patent No.: US 6,392,111 B1
(45) Date of Patent: May 21, 2002

(54) METHOD FOR PRODUCING OLEFINS

(75) Inventors: Manfred T. Reetz; Gunther Lohmer; Renate Lohmer, all of Mülheim an der Ruhr; Elke Westermann, Speyer, all of (DE)

(73) Assignee: Studiengesellschaft Kohle mbH, Mulheim am der Ruhr (DE)

( * ) Notice: Subject to any disclaimer, the term of this patent is extended or adjusted under 35 U.S.C. 154(b) by 0 days.

(21) Appl. No.: 09/787,786

(22) PCT Filed: Sep. 7, 1999

(86) PCT No.: PCT/EP99/06589

§ 371 Date: Mar. 21, 2001

§ 102(e) Date: Mar. 21, 2001

(87) PCT Pub. No.: WO00/17132

PCT Pub. Date: Mar. 30, 2000

(30) Foreign Application Priority Data

Sep. 21, 1998 (DE) .......................... 198 43 012

(51) Int. Cl.$^7$ .......................... C07C 1/27; C07C 255/50; C07C 229/44; C07C 69/76; C07C 209/74
(52) U.S. Cl. .......................... 585/436; 558/378; 560/43; 560/104; 564/409; 568/316; 568/628; 568/928; 570/144
(58) Field of Search .................. 560/43, 104; 558/378; 564/409; 568/316, 628, 928; 570/144; 585/436

(56) References Cited

U.S. PATENT DOCUMENTS 5,703,269 A * 12/1997 Herrmann et al. ............ 560/19

* cited by examiner

*Primary Examiner*—Brian J. Davis
(74) *Attorney, Agent, or Firm*—Norris McLaughlin & Marcus

(57) ABSTRACT

Olefins containing aromatic substituents are synthesized without the addition of phosphonium salts or phosphanes with the aid of a $Pd^{II}$ compound as a catalyst in the presence of nitrogen-containing additives such as N,N-dimethylglycine and a base.

14 Claims, No Drawings

METHOD FOR PRODUCING OLEFINS

This application is a 371 of PCT/EP99/06589 filed Sep. 7, 1999.

The present invention relates to a novel process for the synthesis of olefins having aromatic substituents using a very simple catalyst system.

In industrial chemistry, olefins having aromatic substituents play an important role, e.g., as starting materials for sunscreen agents, polymers, fine chemicals and active substance precursors for pharmaceuticals, plant-protection agents and perfumes.

One possibility for the synthesis of aryl-substituted olefins is the so-called Heck reaction in which iodo-, bromo- or chloroaromatics ArX (X=I, Br, Cl) are reacted with olefins in the presence of stoichiometric amounts of a base and catalytic amounts of a palladium compound, such as $Pd(PPh_3)_4$ (R. F. Heck, "Vinyl Substitutions with Organopalladium Intermediates" in Comprehensive Organic Syntheses, Vol. 4, Pergamon Press, Oxford, 1991, p. 833; R. F. Heck, Palladium Reagents in Organic Syntheses, Academic Press, London, 1985; R. F. Heck, Org. React. (N.Y.) 1982, 27, 345; A. de Meijere, F. E. Meier, Angew. Chem. 1994, 106, 2473; J. Tsuji, Palladium Reagents and Catalysts: Innovations in Organic Synthesis, Wiley, Chichester, 1995). In some cases, triflates ArOTf or diazonium salts $ArN_2^+X^-$ may also be employed (see the above references).

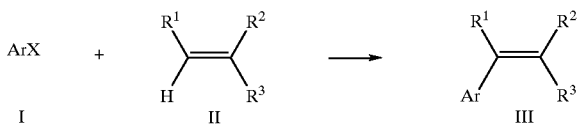

Despite the many publications from university laboratories, the Heck reaction has been used virtually not at all for industrial application to date. This is due to the fact, inter alia, that the reactivity of haloaromatics ArX decreases fast in the order ArI>ArBr>ArCl. Thus, the iodides ArI are mostly employed under relatively mild conditions (80–110° C.). However, such substrates are very expensive. In the case of bromoaromatics, the common catalysts or precatalysts, such as $Pd(PPh_3)_4$, $Pd(OAc)_2$, in the presence of excess $PPh_3$ or $P(tolyl)_3$, result in acceptable yields at reaction temperatures of about 140° C. However, drawbacks include the high amounts of palladium required (1–2 mole percent) and the fact that phosphanes are needed. Therefore, there have been many attempts to develop phosphane-free catalyst systems for Heck reactions. However, despite of a certain progress (A. S. Carlstroem, T. Frejd, J. Org. Chem. 1991, 56, 1289–1293; S. Sengupta, S. Bhattacharya, J. Chem. Soc. Perkin Trans I 1993, 1943–1944; N. A. Bumagin, V. V. Bykov, I. P. Beletskaya, Russ. J. Org. Chem. 1995, 31, 439–444; M. S. Stephan, A. J. J. M. Teunissen, G. K. M. Verzijl, J. G. de Vries, Angew. Chem. 1998, 110, 688–690; Angew. Chem. Int. Ed. Engl. 1998, 37, 662–664; A. F. Shmidt, A. Khalaika, D. -H. Li, Kinet. Catal. 1998, 39, 320; R. Gauler, N. Risch, Eur. J. Org. Chem. 1998, 1193–1200; S. Bräse, J. Rümper, K. Voigt, S. Albecq, G. Thurau, R. Villard, B. Waegell, A. de Meijere, Eur. J. Org. Chem. 1998, 671–678; L. F. Tietze, R. Ferraccioli, Synlett 1998, 145–146; R. L. Augustine, S. T. O'Leary, J. Mol. Catal. A: Chemical 1995, 95, 277–285; M. Beller, K. Küchlein, Synlett 1995, 441–442; S. Sengupta, S. Bhattacharya, J. Chem. Soc. Perkin Trans I 1993, 1943–1944; J. Kiviaho, T. Hanaoka, Y. Kubota, Y. Sugi, J. Mol. Catal. A: Chemical 1995, 101, 25–31), a satisfactory or general catalyst system could not be found. Therefore, more recent works using so-called palladacycles have attracted attention (W. A. Herrmann, C. Brossmer, K. Öfele, C.-P. Reisinger, T. Priermeier, M. Beller, H. Fischer, Angew. Chem. 1995, 107, 1989–1992; Angew. Chem. Int. Ed. Engl. 1995, 34, 1844; W. A. Herrmann, C. Brossmer, C.-P. Reisinger, T. H. Riermeier, K. Öfele, M. Beller, Chem. -Eur. J. 1997, 3, 1357–1364; M. Ohff, A. Ohff, M. E. van der Boom, D. Milstein, J. Am. Chem. Soc. 1997, 119, 11687–11688; DE 44 21 730 C1; EP 0 725 049 A1). Actually, bromoaromatics can be converted smoothly, even with only 0.01 mole percent of palladacycle. However, such catalysts are expensive or require several synthetic steps using the expensive tris(o-tolyl)phosphane or other phosphanes which are difficult to obtain. In the case of certain chloroaromatics, an active catalyst system consisting of $PdCl_2(PhCN)_2$, $Ph_4P^+Cl^-$ and N,N-dimethylglycine (DMG) as an additive was recently described; in the absence of the phosphonium salt $Ph_4P^+Cl^-$, no reaction occurs (M. T. Reetz, G. Lohmer, R. Schwickardi, Angew. Chem. 1998, 110, 492–495; Angew. Chem. Int. Ed. Engl. 1998, 37, 481–483; M. T. Reetz, G. Lohmer, R. Schwickardi DE-A 197 12 388.0, 1997). However, this catalyst system is less suitable for bromoaromatics. Further, phosphonium salts are required, which in turn necessitate the use of phosphanes.

Surprisingly, it has now been found that a strikingly simple, inexpensive and phosphane-free catalyst system causes smooth Heck reactions of bromoaromatics, even when low quantities of the catalyst or precatalyst are employed. The novel catalyst system consists of inexpensive palladium(II) salts in the presence of nitrogen-containing additives, such as N,N-dimethylglycine (DMG), and a base. Thus, the use of phosphanes can be dispensed with.

In addition, it was found that, when very low quantities of simple palladium salts are used, the reaction also proceeds without an additive, though with significantly increased reaction times. Only at concentrations of more than 0.5 mole percent of palladium, the additive has a highly accelerating effect.

As catalysts, there are used common palladium(II) salts PdXY or their $CH_3CN$ or PhCN complexes, wherein typically X=Y=Cl, Br, I, $NO_2$, $RCO_2$ [$R=C_1$–$C_{22}$, $CF_3$, $CCl_3$, $CH_2N(CH_3)_2$, $C_6H_5$] or $RSO_3$ ($R=C_1$–$C_{22}$, $CF_3$, $C_4F_9$, $CCl_3$, $C_6H_5$, p-$CH_3C_6H_4$), or typically X=Cl, Br, I, $RCO_2$ ($R=C_1$–$C_{22}$, $CF_3$, $CCl_3$, $CH_2OCH_3$, $C_6H_5$) and typically Y=$C_6H_5$, o-, m-, p-$CH_3C_6H_4$, o-, m-, p-Cl-$C_6H_4$, o-, m-, p-CHO$C_6H_4$, o-, m-, p-CN-$C_6H_4$, o-, m-, p-$NO_2$-$C_6H_4$, o-, m-, p-PhCO-$C_6H_4$, o-, m-, p-F-$C_6H_4$, 1-$C_{10}H_7$ or 2-$C_{10}H_7$. Preferably, $Pd(OAc)_2$, $PdCl_2(PhCN)_2$, $PdCl_2$, $PdCl_2(CH_3CN)_2$, $C_6H_5PdCl$ or $Pd(NO_3)_2$ or their dimeric or oligomeric forms are used.

As additives, there are used nitrogen-containing carboxylic acids, such as common α- or β-amino acids $H_2N(R)CHCO_2H$ or $H_2N(R)CHCH_2CO_2H$ [R=H, $CH_3$, $C_6H_5$, $CH_2C_6H_4$, $CH(CH_3)_2$], or their N-alkylated forms R'NH(R)CHCO$_2$H or R'NH(R)CHCH$_2$CO$_2$H, or R'$_2$N(R)CHCO$_2$H or R'$_2$N(R)CHCH$_2$CO$_2$H [R'=$CH_3$, $C_2H_5$, $C_3H_7$, $C_4H_9$, or R'+R'=$(CH_2)_4$ or $(CH_2)_5$], or their sodium or potassium salts, anthranilic acid or N,N-dimethylanthranilic acid, or pyridinecarboxylic acids (or their sodium or potassium salts), such as 2-pyridinecarboxylic acid, or aromatic nitrogen-containing heterocycles, such as 2,2'-dipyridyl. Preferably, N,N-di-methylglycine is used. The ratio of additive to palladium ranges between 100:1 and 1:1, preferably between 50:1 and 1:1.

The use of these additives has the effect that the reaction time and reaction temperature can be significantly decreased. Further, such substances increase the selectivity of the reaction.

Aprotic dipolar solvents, such as dimethylformamide (DMF), dimethylacetamide (DMA), dimethyl sulfoxide, propylene carbonate, 1,3-dimethyl-3,4,5,6-tetra-hydro-2(1H)-pyrimidinone (DMPU) or 1-methyl-2-pyrrolidinone (NMP), but also protic solvents, such as methanol, ethanol or diethylene glycol, are used as the solvents. Preferably, DMF, NMP or methanol is used.

Metal salts, such as sodium, potassium, cesium, calcium or magnesium salts of carboxylic acids, or the corresponding carbonates or bicarbonates, or amines, such as triethylamine or trioctylamine, preferably sodium acetate, are used as the base. The ratio of base to aryl halide ranges between 1:1 and 5:1, preferably 1.5:1 to 2:1.

Reaction temperatures of between 60° C. and 180° C. may be selected; preferably, the reactions are allowed to proceed between 100° C. and 140° C.

As to the aryl component ArX, a wide variety of aryl and heteroaryl halides, preferably aryl bromides, but also -O-tosylates, -O-mesylates or -O-triflates may be employed, for example, benzene, naphthalene, pyridine or quinoline derivatives. Aryl diazonium salts may also be reacted.

In the olefin component of the above formula II, $R^1$, $R^2$ and $R^3$ are independently hydrogen, alkyl-$(C_1-C_8)$, phenyl, 1- or 2-naphthyl, vinyl, O-alkyl-$(C_1-C_8)$, O-phenyl, CN, $CO_2H$, $CO_2$-alkyl-$(C_1-C_8)$, $CO_2$-phenyl, $CONH_2$, CONH-alkyl-$(C_1-C_5)$, CON(alkyl)$_2$-$(C_1-C_5)$, fluoro, chloro, PO(phenyl)$_2$, PO(alkyl)$_2$-$(C_1-C_5)$, CO-phenyl, CO-alkyl-$(C_1-C_5)$, NH-alkyl-$(C_1-C_4)$, $SO_3H$, $PO_3H$, $SO_3$-alkyl-$(C_1-C_4)$ or $SO_2$-alkyl-$(C_1-C_4)$; further, cyclic derivatives are also possible, namely if $R^1+R^2=(CH_2)_n$ or $R^2+R^3=(CH_2)_n$, wherein n may be from 2 to 16.

EXAMPLES

Example 1

To a reaction vessel standing on a scale, 5.7 mg (0.015 mmol) of $(C_6H_5CN)_2PdCl_2$ and 30.9 mg (0.3 mmol) of dimethylglycine are added, followed by three cycles of evacuation and flushing with argon. Under argon, 164 mg of anhydrous sodium acetate, 157 mg (1.00 mmol) of bromobenzene and 125 mg (1.2 mmol) of styrene are added. After the addition of 1 ml of NMP, the vessel is sealed, and the mixture is stirred at 130° C. for 10 hours.

After the reaction, the GC standards n-decane and n-hexadecane are added, and 2 ml of diethyl ether is added to the mixture. The suspension is centrifuged, followed by filtering off the solids. Finally, the filtrate is examined by gas chromatography: 98% conversion of bromobenzene; the yield of Heck products was also 98% (selectivity: 96.4% trans-stilbene, 0.6% cis-stilbene, and 3.0% 1,1-diphenylethene).

Example 2

A reaction is performed as described in Example 1, except that methanol is used as the solvent rather than NMP: 99% conversion of bromobenzene; the yield of Heck products was also 99% (selectivity: 97.0% trans-stilbene, 0.5% cis-stilbene, and 2.5% 1,1-diphenylethene).

Example 3

A reaction is performed as described in Example 1, except that diethylene glycol is used as the solvent rather than NMP: 99% conversion of bromobenzene; the yield of Heck products was 98% (selectivity: 96.6%, trans-stilbene, 0.4% cis-stilbene, and 3.0% 1,1-diphenylethene).

Example 4

A reaction is performed as described in Example 1, except that ethanol is used as the solvent rather than NMP: 79% conversion of bromobenzene; the yield of Heck products was 69% (selectivity: 97.0% trans-stilbene, 0.5% cis-stilbene, and 2.5% 1,1-diphenylethene).

Example 5

A reaction is performed as described in Example 1 except that isopropanol is used as the solvent rather than NMP: 60% conversion of bromobenzene; the yield of Heck products was 55% (selectivity: 94.4% trans-stilbene, 2.4% cis-stilbene, and 2.8% 1,1-diphenylethene).

Example 6

A reaction is performed as described in Example 2, except that the catalysis is performed in air: 91% conversion of bromobenzene; the yield of Heck products was 90% (selectivity: 92.1% trans-stilbene, 2.8% cis-stilbene, and 5.1% 1,1-diphenylethene).

Example 7

A reaction is performed as described in Example 1, except that DMA is used as the solvent rather than NMP: 81% conversion of bromobenzene; the yield of Heck products was 78% (selectivity: 96.0% trans-stilbene, 0.9% cis-stilbene, and 3.1% 1,1-diphenylethene).

Example 8

A reaction is performed as described in Example 1, except that DMF is used as the solvent rather than NMP: 54% conversion of bromobenzene; the yield of Heck products was 50% (selectivity: 96.0% trans-stilbene, 0.7% cis-stilbene, and 2.6% 1,1-diphenylethene).

Example 9

A reaction is performed as described in Example 1, except that no dimethylglycine is employed: 40% conversion of bromobenzene; the yield of Heck products was 26% (selectivity: 93.5% trans-stilbene, 0.7% cis-stilbene, and 5.8% 1,1-diphenylethene).

Example 10

A reaction is performed as described in Example 2, except that no dimethylglycine is employed: 8% conversion of bromobenzene; the yield of Heck products was 8% (selectivity: 83.0% trans-stilbene, 8% cis-stilbene, and 9% 1,1-diphenylethene).

Example 11

A reaction is performed as described in Example 3, except that no dimethylglycine is employed: 36% conversion of bromobenzene; the yield of Heck products was 29% (selectivity: 90.0% trans-stilbene, 1.3% cis-stilbene, and 8.7% 1,1-diphenylethene).

Example 12

A reaction is performed as described in Example 2, except that 4.6 mg (0.045 mmol) of dimethylglycine is employed: 99% conversion of bromobenzene; the yield of Heck products was 99% (selectivity: 95.1% trans-stilbene, 0.3% cis-stilbene, and 3.8% 1,1-diphenylethene).

Example 13

A reaction is performed as described in Example 2, except that 10.8 mg (0.11 mmol) of dimethylglycine is employed:

99% conversion of bromobenzene; the yield of Heck products was 99% (selectivity: 96.7% trans-stilbene, 0.3% cis-stilbene, and 3.0% 1,1-diphenylethene).

Example 14

A reaction is performed as described in Example 2, except that 222.5 mg (2.2 mmol) of dimethylglycine is employed: 99% conversion of bromobenzene; the yield of Heck products was 99% (selectivity: 97.2% trans-stilbene, 0.4% cis-stilbene, and 2.4% 1,1-diphenylethene).

Example 15

A reaction is performed as described in Example 1, except that the catalysis is performed in air: 92% conversion of bromobenzene; the yield of Heck products was 89% (selectivity: 96.3% trans-stilbene, 3.1% cis-stilbene, and 0.6% 1,1-diphenylethene).

Example 16

A reaction is performed as described in Example 1, except that 0.38 mg (0.001 mmol) of $PdCl_2(C_6H_5CN)_2$ and 2.1 mg (0.02 mmol) of dimethylglycine are employed: 96% conversion of bromobenzene; the yield of Heck products was 96% (selectivity: 93.7% trans-stilbene, 1.1% cis-stilbene, and 5.2% 1,1-diphenylethene).

Example 17

A reaction is performed as described in Example 1, except that 6.6 g of anhydrous sodium acetate, 6.3 g (40.00 mmol) of bromobenzene and 5.0 g (48 mmol) of styrene are weighed and added under argon. After the addition of 40 ml of NMP, the vessel is sealed, and the mixture is stirred at 130° C. for 10 hours: 99% conversion of bromobenzene; the yield of Heck products was 95% (selectivity: 93.3% trans-stilbene, 0.7% cis-stilbene, and 6.0% 1,1-diphenylethene).

Example 18

A reaction is performed as described in Example 1, except that 1.0 ml of a palladium stock solution (3.8 mg [0.01 mmol] of $PdCl_2(C_6H_5CN)_2$/20.4 mg [0.2 mmol] of dimethylglycine in 100 ml of methanol/dichloromethane) instead of $PdCl_2(C_6H_5CN)_2$ and dimethylglycine is weighed and added in air. The mixture is stirred at 130° C. for 24 hours: 98% conversion of bromobenzene; the yield of Heck products was 97% (selectivity: 92.7% trans-stilbene, 0.7% cis-stilbene, and 6.6% 1,1-diphenylethene).

Example 19

A reaction is performed as described in Example 1, except that 0.1 ml of a palladium stock solution (3.8 mg [0.01 mmol] of $PdCl_2(C_6H_5CN)_2$/20.4 mg [0.2 mmol] of dimethylglycine in 100 ml of methanol/dichloromethane) instead of $PdCl_2(C_6H_5CN)_2$ and dimethylglycine is weighed and added in air. The mixture is stirred at 130° C. for 96 hours: 96% conversion of bromobenzene; the yield of Heck products was 91% (selectivity: 92.9% trans-stilbene, 0.7% cis-stilbene, and 6.4% 1,1-diphenylethene).

Example 20

A reaction is performed as described in Example 2, except that 3.4 mg (0.015 mmol) of $Pd(OAc)_2$ and no dimethylglycine are weighed and added: 8% conversion of bromobenzene; the yield of Heck products was also 8%.

Example 21

A reaction is performed as described in Example 1, except that 3.4 mg (0.015 mmol) of $Pd(OAc)_2$ and no dimethylglycine are weighed and added: 18% conversion of bromobenzene; the yield of Heck products was 15% (selectivity: 94.0% trans-stilbene, 0.8% cis-stilbene, and 5.2% 1,1-diphenylethene).

Example 22

A reaction is performed as described in Example 1, except that 3.4 mg (0.015 mmol) of $Pd(OAc)_2$ and no dimethylglycine are weighed and added, and 1 ml of DMSO is added rather than NMP: 38% conversion of bromobenzene; the yield of Heck products was 32% (selectivity: 93.0% trans-stilbene, 1.0% cis-stilbene, and 6.0% 1,1-diphenylethene).

Example 23

A reaction is performed as described in Example 1, except that 3.4 mg (0.015 mmol) of $Pd(OAc)_2$ and no dimethylglycine are weighed and added, and 1 ml of acetonitrile is added rather than NMP: 2% conversion of bromobenzene.

Example 24

A reaction is performed as described in Example 22, except that the mixture is stirred at 130° C. for 30 hours: 51% conversion of bromobenzene; the yield of Heck products was 41% (selectivity: 93.0% trans-stilbene, 1.0% cis-stilbene, and 6.0% 1,1-diphenylethene).

Example 25

A reaction is performed as described in Example 22, except that the mixture is stirred at 150° C. for 30 hours: 70% conversion of bromobenzene; the yield of Heck products was 65% (selectivity: 92.0% trans-stilbene, 1.0% cis-stilbene, and 7.0% 1,1-diphenylethene).

Example 26

A reaction is performed as described in Example 21, except that 1.0 ml of a palladium stock solution (2.2 mg [0.01 mmol] of $Pd(OAc)_2$ in 100 ml of methanol/dichloromethane) instead of $Pd(OAC)_2$ is weighed and added in air. The mixture is stirred at 130° C. for 24 hours: 77% conversion of bromobenzene; the yield of Heck products was 89% (selectivity: 92.7% trans-stilbene, 0.8% cis-stilbene, and 6.5% 1,1-diphenylethene).

Example 27

A reaction is performed as described in Example 21, except that 0.1 ml of a palladium stock solution (2.2 mg [0.01 mmol] of $Pd(OAc)_2$ in 100 ml of methanol/dichloromethane) instead of $Pd(OAc)_2$ is weighed and added in air. The mixture is stirred at 130° C. for 96 hours: 85% conversion of bromobenzene; the yield of Heck products was 85% (selectivity: 93.0% trans-stilbene, 0.7% cis-stilbene, and 6.3% 1,1-diphenylethene).

Example 28

A reaction is performed as described in Example 1, except that 36.9 mg (0.3 mmol) of picolinic acid instead of dimethylglycine is weighed and added: 36% conversion of bromobenzene; the yield of Heck products was 35% (selectivity: 97.3% trans-stilbene, 0.6% cis-stilbene, and 2.1% 1,1-diphenylethene).

Example 29

A reaction is performed as described in Example 1, except that 36.9 mg (0.3 mmol) of isonicotinic acid instead of dimethylglycine is weighed and added: 76% conversion of bromobenzene; the yield of Heck products was 74% (selectivity: 91.0% trans-stilbene, 0.7% cis-stilbene, and 8.6% 1,1-diphenylethene).

Example 30

A reaction is performed as described in Example 1, except that 22.5 mg (0.3 mmol) of glycine instead of dimethylglycine is weighed and added: 90% conversion of bromobenzene; the yield of Heck products was 83% (selectivity: 92.9% trans-stilbene, 0.7% cis-stilbene, and 6.4% 1,1-diphenylethene).

Example 31

A reaction is performed as described in Example 1, except that 187.0 mg (1.0 mmol) of 4-bromoanisole instead of bromobenzene is weighed and added: 89% conversion of bromoanisole; the yield of Heck products was 89% (selectivity: 95.0% (E)-4-methoxystilbene).

Example 32

A reaction is performed as described in Example 1, except that 187.0 mg (1.0 mmol) of 3-bromoanisole instead of bromobenzene is weighed and added: 60% conversion of bromoanisole; the yield of Heck products was 60% (selectivity: 96.0% (E)-3-methoxystilbene).

Example 33

A reaction is performed as described in Example 1, except that 187.0 mg (1.0 mmol) of 2-bromoanisole instead of bromobenzene is weighed and added: 22% conversion of bromoanisole; the yield of Heck products was 22% (selectivity: 100% (E)-2-methoxystilbene).

Example 34

A reaction is performed as described in Example 1, except that 201.6 mg (1.0 mmol) of 4-bromonitrobenzene instead of bromobenzene is weighed and added: 100% conversion of bromonitrobenzene; the yield of Heck products was 74% (selectivity: 97.0% (E)-4-nitrostilbene).

Example 35

A reaction is performed as described in Example 1, except that 225.0 mg (1.0 mmol) of 4-bromobenzotrifluoride instead of bromobenzene is weighed and added: 96% conversion of bromobenzotrifluoride; the yield of Heck products was 96% (selectivity: 96.0% (E)-4-trifluoromethylstilbene).

Example 36

A reaction is performed as described in Example 1, except that 200.1 mg (1.0 mmol) of 4-N,N-dimethylbromoaniline instead of bromobenzene is weighed and added: 60% conversion of N,N-dimethylbromoaniline; the yield of Heck products was 60% (selectivity: 94.0%(E)-4-N,N-dimethylaminostilbeie).

Example 37

A reaction is performed as described in Example 1, except that 182.0 mg (1.0 mmol) of 4-bromobenzonitrile instead of bromobenzene is weighed and added: 100% conversion of bromobenzonitrile; the yield of Heck products was 100% (selectivity: 96.0% (E)-4-cyanostilbene).

Example 38

A reaction is performed as described in Example 1, except that 199.0 mg (1.0 mmol) of 4-bromoacetophenone instead of bromobenzene is weighed and added: 100% conversion of bromoacetophenone; the yield of Heck products was 100% (selectivity: 96.0% (E)-4-acetylstilbene).

Example 39

A reaction is performed as described in Example 1, except that the mixture is stirred at 110° C. for 10 hours: 98% conversion of bromobenzene; the yield of Heck products was 98% (selectivity: 96.6% trans-stilbene, 0.4% cis-stilbene, and 3.0% 1,1-diphenylethene).

Example 40

A reaction is performed as described in Example 1, except that 2.7 mg (0.015 mmol) of $PdCl_2$ instead of $PdCl_2(C_6H_5CN)_2$ is weighed and added: 99% conversion of bromobenzene; the yield of Heck products was 99% (selectivity: 96.0% trans-stilbene, 0.6% cis-stilbene, and 3.4% 1,1-diphenylethene).

Example 41

A reaction is performed as described in Example 1, except that 4.0 mg (0.015 mmol) of $Pd(NO_3)_2 \cdot 2H_2O$ instead of $PdCl_2(C_6H_5CN)_2$ is weighed and added: 70% conversion of bromobenzene; the yield of Heck products was 62% (selectivity: 96.0% trans-stilbene, 0.6% cis-stilbene, and 3.3% 1,1-diphenylethene).

Example 42

A reaction is performed as described in Example 1, except that 3.4 mg (0.015 mmol) of $Pd(OAc)_2$ instead of $PdCl_2(C_6H_5CN)_2$ is weighed and added: 100% conversion of bromobenzene; the yield of Heck products was 95% (selectivity: 95.7% trans-stilbene, 0.6% cis-stilbene, and 3.6% 1,1-diphenylethene).

Example 43

A reaction is performed as described in Example 1, except that 221.2 mg (1.2 mmol) of ethylhexyl acrylate instead of styrene is weighed and added: 97% conversion of bromobenzene; the yield of Heck products was 97% (selectivity: 98.4% trans product).

Example 44

A reaction is performed as described in Example 1, except that 153.6 mg (1.2 mmol) of butyl acrylate instead of styrene is weighed and added: 96% conversion of bromobenzene; the yield of Heck products was 92% (selectivity: 99.0% trans product).

Example 45

A reaction is performed as described in Example 1, except that 221.2 mg (1.2 mmol) of ethylhexyl acrylate instead of styrene and 187 mg (1.00 mmol) of 4-bromoanisole is weighed and added: 97% conversion of bromoanisole; the yield of Heck products was 97% (selectivity: 97.0% trans product).

Example 46

A reaction is performed as described in Example 1, except that 153.6 mg (1.2 mmol) of butyl acrylate instead of styrene and 187 mg (1.00 mmol) of 4-bromoanisole is weighed and added: 98% conversion of bromoanisole; the yield of Heck products was 78% (selectivity: 99.0% trans product).

Example 47

A reaction is performed as described in Example 1, except that 0.0009 mole percent of $Pd(OAc)_2$ is employed in the absence of a nitrogen-containing additive, and a reaction time of 96 hours is chosen: 85% conversion of bromobenzene; the yield of Heck products was 80% (selectivity: 93% trans-stilbene, 0.7% cis-stilbene, and 6.3% 1,1-diphenylethene).

What is claimed is:

1. A process for the preparation of olefin-substituted aromatics or heteroaromatics of formula III

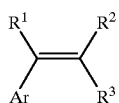

III wherein Ar represents substituted or unsubstituted aryl or heteroaryl residues, and $R^1$, $R^2$ and $R^3$ independently represent hydrogen, alkyl-$(C_1-C_8)$, phenyl, 1- or 2-naphthyl, vinyl, O-alkyl-$(C_1-C_8)$, O-phenyl, CN, $CO_2H$, $CO_2$-alkyl-$(C_1-C_8)$, $CO_2$-phenyl, $CONH_2$, CONH-alkyl-$(C_1-C_5)$, CON(alkyl)$_2$-$(C_1-C_5)$, fluoro, chloro, PO(phenyl)$_2$, PO(alkyl)$_2$-$(C_1-C_5)$, CO-phenyl, CO-alkyl-$(C_1-C_5)$, NH-alkyl-$(C_1-C_4)$, $SO_3H$, $PO_3H$, $SO_3$-alkyl-$(C_1-C_4)$ or $SO_2$-alkyl-$(C_1-C_4)$, or $R^1+R^2=(CH_2)_n$, or $R^2+R^3=(CH_2)_n$ wherein n=2–16, by reacting aromatics or heteroaromatics of formula I ArX

I wherein Ar has the same meaning as in formula III and X represents chloro, bromo, $OSO_2CH_3$, $OSO_2$-tolyl, $OSO_2CF_3$ or $OSO_2C_4F_9$ or $N_2^{+Cl-}$, with olefins of formula II

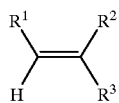

II wherein $R^1$, $R^2$ and $R^3$ have the same meanings as in formula III, in the presence of palladium catalysts, characterized in that a palladium(II) compound of general formula PdXY or its $CH_3CN$ or $C_6H_5CN$ complexes, wherein X=Y=Cl, Br, I, $NO_3$, $RCO_2$ (R=$C_1$–$C_{22}$, $CF_3$, $CCl_3$, $CH_2OCH_3$, $C_6H_5$) or $RSO_3$ (R=$C_1$–$C_{22}$, $CF_3$, $C_4F_9$, $CCl_3$, $C_6H_5$, p-$CH_3C_6H_4$), is used as the catalyst, and the reaction is performed in the absence of phosphonium salts and phosphanes and in the presence of a nitrogen-containing additive and a solvent and a base at temperatures of from 60° C. to 180° C.

2. The process according to claim 1, wherein an α-amino acid is used as said nitrogen-containing additive.

3. The process according to claim 1, wherein the N-alkylated form of an α-amino acid is used as said additive.

4. The process according to claim 3, wherein N,N-dimethylglycine is used as said additive.

5. The process according to claim 1, wherein a heterocyclic compound is used as said additive.

6. The process according to claim 5, wherein 2,2'-dipyridyl is used as said additive.

7. The process according to claim 1, wherein the ratio of palladium to the nitrogen-containing additive is from 1:3 to 1:100.

8. The process according to claim 1, wherein the amount of said palladium catalyst is from 0.001 to 3 mole percent.

9. The process according to claim 1, wherein a dipolar aprotic solvent is used as said solvent.

10. The process according to claim 9, wherein dimethyl sulfoxide, dimethyl-formamide, dimethylacetamide, 1,3-dimethyl-3,4,5,6-tetrahydro-2(1H)-pyrimidone or N-methylpyrrolidone is used as said dipolar aprotic solvent.

11. The process according to claim 1, wherein a protic solvent is used as said solvent.

12. The process according to claim 11, wherein methanol, ethanol or diethylene glycol is used as said protic solvent.

13. The process according to claim 1, wherein an amine, an alkali or alkaline earth metal salt of a carboxylic acid or an alkali or alkaline earth metal carbonate or bicarbonate is used as said base.

14. The process according to claim 1, wherein the reaction is performed in a temperature range of from 100 to 140° C.

* * * * *